United States Patent
Mahe et al.

(10) Patent No.: US 6,455,054 B2
(45) Date of Patent: *Sep. 24, 2002

(54) TREATING SKIN AFFLICTIONS/ CONDITIONS WITH 2-AMINO-4-ALKYLAMINOPYRIMIDINE 3-OXIDE COMPOUNDS

(75) Inventors: Yann Mahe, Morsang sur Orge; Jean-François Michelet, Creteil; Lionel Breton, Versailles, all of (FR)

(73) Assignee: Societe l'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/438,522

(22) Filed: Nov. 12, 1999

(30) Foreign Application Priority Data

Nov. 12, 1998 (FR) .............................. 98 14211

(51) Int. Cl.$^7$ ................................ A61K 7/00
(52) U.S. Cl. ................ 424/401; 424/70.1; 514/269; 514/880
(58) Field of Search ................ 424/70.1; 514/880, 514/269, 320, 323

(56) References Cited

U.S. PATENT DOCUMENTS 5,328,914 A * 7/1994 Hocaquaux et al. ........ 514/310

FOREIGN PATENT DOCUMENTS

| EP | 0356271 | 2/1990 |
| EP | 0522964 | 1/1993 |
| EP | 0736300 | 10/1996 |

OTHER PUBLICATIONS

Mahe, Yann et al "Aminoxidil–related compound . . . ", Skin Pharmacol (1996), 9(3), 177–183, Coden: Skpheu; ISSN: 1011–0283.

* cited by examiner

Primary Examiner—Jose' G. Dees
Assistant Examiner—Konata M George
(74) Attorney, Agent, or Firm—Burns, Doane, Swecker & Mathis, L.L.P.

(57) ABSTRACT

Skin-soothing, -calmant and/or anti-inflammatory amounts of at least one 2-amino-4-alkylaminopyrimidine 3-oxide are well suited for therapeutically treating such afflictions/conditions of human skin as sensitive skin, skin discomfort, tautness, itchiness or swelling of the skin, blotchy red skin, or sensations of warming or burning of the skin.

18 Claims, No Drawings

TREATING SKIN AFFLICTIONS/CONDITIONS WITH 2-AMINO-4-ALKYLAMINOPYRIMIDINE 3-OXIDE COMPOUNDS

CROSS-REFERENCE TO PRIORITY APPLICATION

This application claims priority under 35 U.S.C. §119 of FR-98/14211, filed Nov. 12, 1998, hereby expressly incorporated by reference.

BACKGROUND OF THE INVENTION

1. Technical Field of the Invention

The present invention relates to treating, for example soothing or calming, a variety of skin afflictions/conditions by administering to a candidate individual in need of such treatment an effective amount of at least one 2-amino-4-alkylaminopyrimidine 3-oxide compound.

2. Description of the Prior Art

It is known to this art that humans are subject to adverse cutaneous challenges or stimuli which are characterized by a sensation of skin discomfort, tautness, itchiness, a sensation of burning or warmth on the skin, or red blotches.

Active agents for controlling these types of conditions/afflictions have long been sought by researchers in this art.

Although various active agents have already been proposed, a constant interest remains to develop alternatives providing improved skin-soothing/calmant or anti-inflammatory activity, in particular for treating minor skin afflictions/conditions, such as, for example, sensitive skin, skin discomfort, tautness of the skin, itchiness of the skin, swelling of the skin, red blotchy skin or a sensation of burning or warmth on the skin.

SUMMARY OF THE INVENTION

Accordingly, a major object of the present invention is the provision of improved regime/regimen for treating and alleviating the symptoms of a variety of objectionable skin afflictions/conditions, while at the same time avoiding any appreciable side effects.

Briefly, the present invention features treating the aforesaid skin conditions/afflictions with a skin-soothing, -calmant or anti-inflammatory effective amount of at least one 2-amino-4-alkylaminopyrimidine 3-oxide compound formulated into a physiologically acceptable medium therefor.

DETAILED DESCRIPTION OF BEST MODE AND SPECIFIC/PREFERRED EMBODIMENTS OF THE INVENTION

More particularly according to the present invention, by the expression "physiologically acceptable medium" is intended a medium (e.g., vehicle, diluent or carrier) which is compatible with the skin, the mucous membranes, the nails and the hair of a human subject (hereinafter, simply the skin and/or the scalp).

The compounds of the 2-amino-4-alkylaminopyrimidine 3-oxide family which are well suited for administration according to the invention have the general formula (I):

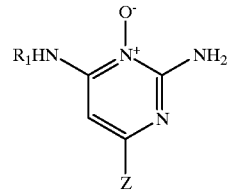

in which $R_1$ is an alkyl radical having from 1 to 20 carbon atoms, and Z is a hydrogen atom or a radical —$OR_2$, wherein $R_2$ is an alkyl radical having from 1 to 12 carbon atoms, as well as the acyl derivatives and acid addition salts thereof.

According to the invention, by the expression "alkyl radical" is intended a linear or branched acyclic radical originating via the removal of a hydrogen atom from the molecule of a hydrocarbon, such as, for example, a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or eicosadecyl radical.

In one preferred embodiment of the invention, $R_1$ is an alkyl radical having from 6 to 12 carbon atoms, such as, for example, a hexyl, heptyl, octyl, nonyl, decyl, undecyl or dodecyl radical.

In another preferred embodiment of the invention, $R_2$ is an alkyl radical having from 2 to 6 carbon atoms, such as, for example, an ethyl, propyl, butyl, pentyl or hexyl radical.

Preferred compounds according to the invention include:

2-amino-4-methylaminopyrimidine 3-oxide;
2-amino-4-ethylaminopyrimidine 3-oxide;
2-amino-4-propylaminopyrimidine 3-oxide;
2-amino-4-butylaminopyrimidine 3-oxide;
2-amino-4-pentylaminopyrimidine 3-oxide;
2-amino-4-hexylaminopyrimidine 3-oxide;
2-amino-4-heptylaminopyrimidine 3-oxide;
2-amino-4-octylaminopyrimidine 3-oxide;
2-amino-4-nonylaminopyrimidine 3-oxide;
2-amino-4-decylaminopyrimidine 3-oxide;
2-amino-4-undecylaminopyrimidine 3-oxide;
2-amino-4-dodecylaminopyrimidine 3-oxide;
2-amino-4-tridecylaminopyrimidine 3-oxide;
2-amino-4-tetradecylaminopyrimidine 3-oxide;
2-amino-4-pentadecylaminopyrimidine 3-oxide;
2-amino-4-hexadecylaminopyrimidine 3-oxide;
2-amino-4-heptadecylaminopyrimidine 3-oxide;
2-amino-4-octadecylaminopyrimidine 3-oxide;
2-amino-4-nonadecylaminopyrimidine 3-oxide;
2-amino-4-eicosadecylaminopyrimidine 3-oxide;
2-amino-4-methylamino-6-methoxypyrimidine 3-oxide;
2-amino-4-ethylamino-6-methoxypyrimidine 3-oxide;
2-amino-4-propylamino-6-methoxypyrimidine 3-oxide;
2-amino-4-butylamino-6-methoxypyrimidine 3-oxide;
2-amino-4-pentylamino-6-methoxypyrimidine 3-oxide;
2-amino-4-hexylamino-6-methoxypyrimidine 3-oxide;
2-amino-4-heptylamino-6-methoxypyrimidine 3-oxide;
2-amino-4-octylamino-6-methoxypyrimidine 3-oxide;
2-amino-4-nonylamino-6-methoxypyrimidine 3-oxide;
2-amino-4-decylamino-6-methoxypyrimidine 3-oxide;
2-amino-4-undecylamino-6-methoxypyrimidine 3-oxide;
2-amino-4-dodecylamino-6-methoxypyrimidine 3-oxide;
2-amino-4-tridecylamino-6-methoxypyrimidine 3-oxide;
2-amino-4-tetradecylamino-6-methoxypyrimidine 3-oxide;

2-amino-4-pentadecylamino-6-methoxypyrimidine 3-oxide;
2-amino-4-hexadecylamino-6-methoxypyrimidine 3-oxide;
2-amino-4-heptadecylamino-6-methoxypyrimidine 3-oxide;
2-amino-4-octadecylamino-6-methoxypyrimidine 3-oxide;
2-amino-4-nonadecylamino-6-methoxypyrimidine 3-oxide;
2-amino-4-eicosadecylamino-6-methoxypyrimidine 3-oxide;
2-amino-4-methylamino-6-ethoxypyrimidine 3-oxide;
2-amino-4-ethylamino-6-ethoxypyrimidine 3-oxide;
2-amino-4-propylamino-6-ethoxypyrimidine 3-oxide;
2-amino-4-butylamino-6-ethoxypyrimidine 3-oxide;
2-amino-4-pentylamino-6-ethoxypyrimidine 3-oxide;
2-amino-4-hexylamino-6-ethoxypyrimidine 3-oxide;
2-amino-4-heptylamino-6-ethoxypyrimidine 3-oxide;
2-amino-4-octylamino-6-ethoxypyrimidine 3-oxide;
2-amino-4-nonylamino-6-ethoxypyrimidine 3-oxide;
2-amino-4-decylamino-6-ethoxypyrimidine 3-oxide;
2-amino-4-undecylamino-6-ethoxypyrimidine 3-oxide;
2-amino-4-dodecylamino-6-ethoxypyrimidine 3-oxide;
2-amino-4-tridecylamino-6-ethoxypyrimidine 3-oxide;
2-amino-4-tetradecylamino-6-ethoxypyrimidine 3-oxide;
2-amino-4-pentadecylamino-6-ethoxypyrimidine 3-oxide;
2-amino-4-hexadecylamino-6-ethoxypyrimidine 3-oxide;
2-amino-4-heptadecylamino-6-ethoxypyrimidine 3-oxide;
2-amino-4-octadecylamino-6-ethoxypyrimidine 3-oxide;
2-amino-4-nonadecylamino-6-ethoxypyrimidine 3-oxide;
2-amino-4-eicosadecylamino-6-ethoxypyrimidine 3-oxide;
2-amino-4-methylamino-6-propyloxypyrimidine 3-oxide;
2-amino-4-ethylamino-6-propyloxypyrimidine 3-oxide;
2-amino-4-propylamino-6-propyloxypyrimidine 3-oxide;
2-amino-4-butylamino-6-propyloxypyrimidine 3-oxide;
2-amino-4-pentylamino-6-propyloxypyrimidine 3-oxide;
2-amino-4-hexylamino-6-propyloxypyrimidine 3-oxide;
2-amino-4-heptylamino-6-propyloxypyrimidine 3-oxide;
2-amino-4-octylamino-6-propyloxypyrimidine 3-oxide;
2-amino-4-nonylamino-6-propyloxypyrimidine 3-oxide;
2-amino-4-decylamino-6-propyloxypyrimidine 3-oxide;
2-amino-4-undecylamino-6-propyloxypyrimidine 3-oxide;
2-amino-4-dodecylamino-6-propyloxypyrimidine 3-oxide;
2-amino-4-tridecylamino-6-propyloxypyrimidine 3-oxide;
2-amino-4-tetradecylamino-6-propyloxypyrimidine 3-oxide;
2-amino-4-pentadecylamino-6-propyloxypyrimidine 3-oxide;
2-amino-4-hexadecylamino-6-propyloxypyrimidine 3-oxide;
2-amino-4-heptadecylamino-6-propyloxypyrimidine 3-oxide;
2-amino-4-octadecylamino-6-propyloxypyrimidine 3-oxide;
2-amino-4-nonadecylamino-6-propyloxypyrimidine 3-oxide;
2-amino-4-eicosadecylamino-6-propyloxypyrimidine 3-oxide;
2-amino-4-methylamino-6-butyloxypyrimidine 3-oxide;
2-amino-4-ethylamino-6-butyloxypyrimidine 3-oxide;
2-amino-4-propylamino-6-butyloxypyrimidine 3-oxide;
2-amino-4-butylamino-6-butyloxypyrimidine 3-oxide;
2-amino-4-pentylamino-6-butyloxypyrimidine 3-oxide;
2-amino-4-hexylamino-6-butyloxypyrimidine 3-oxide;
2-amino-4-heptylamino-6-butyloxypyrimidine 3-oxide;
2-amino-4-octylamino-6-butyloxypyrimidine 3-oxide;
2-amino-4-nonylamino-6-butyloxypyrimidine 3-oxide;
2-amino-4-decylamino-6-butyloxypyrimidine 3-oxide;
2-amino-4-undecylamino-6-butyloxypyrimidine 3-oxide;
2-amino-4-dodecylamino-6-butyloxypyrimidine 3-oxide;
2-amino-4-tridecylamino-6-butyloxypyrimidine 3-oxide;
2-amino-4-tetradecylamino-6-butyloxypyrimidine 3-oxide;
2-amino-4-pentadecylamino-6-butyloxypyrimidine 3-oxide;
2-amino-4-hexadecylamino-6-butyloxypyrimidine 3-oxide;
2-amino-4-heptadecylamino-6-butyloxypyrimidine 3-oxide;
2-amino-4-octadecylamino-6-butyloxypyrimidine 3-oxide;
2-amino-4-nonadecylamino-6-butyloxypyrimidine 3-oxide;
2-amino-4-eicosadecylamino-6-butyloxypyrimidine 3-oxide; and the branched isomers thereof.

More preferred compounds according to the invention include:
2-amino-4-hexylaminopyrimidine 3-oxide;
2-amino-4-octylaminopyrimidine 3-oxide;
2-amino-4-dodecylaminopyrimidine 3-oxide;
2-amino-4-octylamino-6-butyloxypyrimidine 3-oxide.

Even more preferred are 2-amino-4-dodecylaminopyrimidine 3-oxide, and 2-amino-4-octylamino-6-butyloxypyrimidine 3-oxide.

It will of course be appreciated that the subject 2-amino-4-alkylaminopyrimidine 3-oxide compounds can be administered either alone or in admixture.

In another embodiment of the invention compositions are formulated, in a physiologically acceptable medium therefor, comprising an effective amount of at least one 2-amino-4-alkylaminopyrimidine 3-oxide compound having the general formula (I), such compound or composition being well suited for controlling or alleviating the symptoms of sensitive skin, skin disruptions, such as skin discomfort, tautness of the skin, itchiness of the skin, swelling of the skin, blotchy red skin or a sensation of burning or warming of the skin.

The compositions of the invention comprising at least one 2-amino-4-alkylaminopyrimidine 3-oxide compound are well suited for cosmetic applications.

The amount of the 2-amino-4-alkylaminopyrimidine 3-oxide compound required according to the invention of course depends on the desired effect and should be an amount which is effective for controlling the objectionable skin disruptions sought to be treated.

By way of example, the amount of compounds of the 2-amino-4-alkylaminopyrimidine 3-oxide family which are advantageously administered according to the invention typically ranges, for example, from 0.01% to 20% and preferably from 0.05% to 10% of the total weight of the composition.

The subject compositions are conveniently administered via any route, preferably via topical application onto the skin.

The physiologically acceptable medium (vehicle, diluent or carrier) into which the 2-amino-4-alkylaminopyrimidine 3-oxide compound is formulated according to the invention may be anhydrous or aqueous. By the expression "anhydrous medium" is intended a solvent medium containing less than 1% water. This medium is advantageously a solvent or mixture of solvents selected, in particular, from among $C_2$-$C_4$ lower alcohols, for example ethyl alcohol, alkylene glycols, for example propylene glycol, and alkylene glycol or dialkylene glycol alkyl ethers, in which the alkyl or alkylene radicals contain from 1 to 4 carbon atoms. By the expression "aqueous medium" is intended a medium advantageously of water or a mixture of water and another physiologically acceptable solvent, selected in particular from among the organic solvents indicated above. In the latter event, these other solvents, when they are indeed present, constitute about 5% to 95% by weight of the composition.

It is possible for the physiologically acceptable medium to contain other additives and adjuvants commonly formulated into cosmetics, such as surfactants, thickeners or gelling agents, cosmetic agents, preservatives or acidifying or basifying agents that are per se well known to this art, and in amounts which are sufficient to provide the desired physical state, in particular the form of a more or less thickened lotion, a gel, an emulsion or a cream. These can optionally be provided in a form pressurized as an aerosol or vaporized from a pump-dispenser bottle.

According to the invention, the subject compositions can comprise at least one compound of formula (I) with other active agents. Exemplary such other active agents include:

(a) other skin-soothing agents or calmants, for instance peptides such as, for example, the tripeptide lysine-proline-valine;

(b) keratolytic agents such as α- and β-hydroxycarboxylic acids or β-ketocarboxylic acids, their salts, amides or esters and, more particularly, hydroxy acids such as glycolic acid, lactic acid, salicylic acid, citric acid and fruit acids in general, and 5-n-octanoylsalicylic acid;

(c) free-radical scavengers, such as α-tocopherol or esters thereof, superoxide dismutases, certain metal-chelating agents or ascorbic acid and esters thereof;

(d) extracts of plant, marine or bacterial origin.

Other compounds can also be thus formulated, namely, for example, phospholipids such as lecithin, linoleic acid, linolenic acid, salicylic acid and the derivatives thereof described in FR-2,581,542, such as salicylic acid derivatives bearing an alkanoyl group substituent having from 2 to 12 carbon atoms in position 5 of the benzene ring, hydroxycarboxylic or ketocarboxylic acids and esters thereof, carotenoids, eicosatetraenoic acid and eicosatrienoic acid or the esters and amides thereof, and vitamin D and derivatives thereof.

The 2-amino-4-alkylaminopyrimidine 3-oxide compound, or cosmetic composition comprised thereof, is most conveniently topically applied onto those areas of the skin and/or the scalp of an individual requiring such treatment, optionally maintained in contact therewith for several hours and optionally rinsed therefrom.

Thus, the present invention also features a skin-soothing or calmant cosmetic regime/regimen for treating sensitive skin, skin disruptions such as skin discomfort, tautness of the skin, itchiness of the skin, swelling of the skin, blotchy red skin or a burning sensation or sensation of warmth on the skin, entailing topically applying a cosmetic composition comprising at least one 2-amino-4-alkylaminopyrimidine 3-oxide compound onto the skin and/or the scalp of an individual in need of such treatment, maintaining such composition in contact with the skin and/or the scalp for such period of time as required to elicit the desired therapeutic/anti-inflammatory effect, and optionally rinsing the composition therefrom.

Such cosmetic treatment permits enhancing the aesthetics and comfort of the skin and/or the scalp and enhancing an individual's comfort by treating/alleviating the effects of adverse challenges on the skin.

In order to further illustrate the present invention and the advantages thereof, the following specific examples are given, it being understood that same are intended only as illustrative and in nowise limitative.

EXAMPLES

The following are specific examples of compositions according to the present invention; each was formulated by simply intimately admixing the various constituents thereof.

Lotion:

| Lotion: | |
|---|---|
| 2-Amino-4-dodecylaminopyrimidine 3-oxide | 1.500% |
| Propylene glycol | 10.000% |
| Isopropyl alcohol qs | 100% |

1 ml of this lotion is applied to the scalp at a rate of once or twice a day.

| Gel: | | |
|---|---|---|
| Chimexane NS[1] | | 1.800% |
| Monosodium stearoylglutamate | | 0.200% |
| 2-Amino-4-octylamino-6-butyloxypyrimidine 3-oxide | | 2.000% |
| Carbomer | | 0.200% |
| Triethanolamine | qs | pH = 7 |
| Preservatives | qs | |
| Fragrances | qs | |
| Demineralized water | qs | 100% |

This gel is applied to the skin once or twice a day.

| Lotion: | | |
|---|---|---|
| 2-Amino-4-dodecylaminopyrimidine 3-oxide | | 1.000% |
| Propylene glycol | | 30.000% |
| Ethyl alcohol | | 40.500% |
| Water | qs | 100% |

This lotion is applied once or twice a day, at a rate of 1 ml per application.

| Thickened lotion: | | |
|---|---|---|
| 2-Amino-4-octylaminopyrimidine 3-oxide | | 2.000% |
| Kawaine | | 2.000% |
| Hydroxypropylcellulose marketed by Hercules under the trademark Klucel G[1] | | 3.500% |
| Ethyl alcohol | qs | 100% |

This thickened lotion is applied once or twice a day.

| Lotion: | | |
|---|---|---|
| Chimexane NL[1] | | 0.475% |
| Cholesterol | | 0.475% |
| Monosodium stearoylglutamate | | 0.050% |
| 2-Amino-4-dodecylaminopyrimidine 3-oxide | | 0.500% |
| Preservatiges | qs | |
| Dyes | qs | |
| Fragrances | qs | |
| Demineralized water | qs | 100% |

This lotion is applied once or twice a day, at a rate of 1 ml per application.

| Lotion: | |
|---|---|
| 2-Amino-4-hexylaminopyrimidine 3-oxide | 0.100% |
| Propylene glycol monomethyl ether marketed under the trademark Dowanol PM[1] by Dow Chemical | 20.000% |
| Hydroxypropylcellulose marketed by Hercules under the trademark Klucel G[1] | 3.000% |
| Ethyl alcohol | 40.000% |
| Water        qs | 100% |

This thickened lotion is applied at a rate of 1 ml per application.

| Day cream: | |
|---|---|
| 2-Amino-4-dodecylaminopyrimidine 3-oxide | 1.000% |
| Sucrose stearate | 4.000% |
| Stearyl alcohol | 2.000% |
| Cyclohexasiloxane | 9.000% |
| Mineral oil | 4.000% |
| Glycerol | 5.000% |
| Xanthan gum | 0.300% |
| Carbomer | 0.500% |
| Preservatives | 0.300% |
| Fragrances | 0.300% |
| Water        qs | 100% |
| Care fluid: | |
| 2-Amino-4-dodecylaminopyrimidine 3-oxide | 1.000% |
| Stearyl alcohol | 0.400% |
| Sorbitan stearate | 1.500% |
| Glycerol | 5.000% |
| Xanthan gum | 0.200% |
| Carbomer | 0.100% |
| Cyclohexasiloxane | 7.000% |
| Preservatives | 0.300% |
| Fragrances | 0.200% |
| Water        qs | 100% |
| Lotion: | |
| 2-Amino-4-dodecylaminopyrimidine 3-oxide | 0.500% |
| Propylene glycol | 2.000% |
| Extract of cornflower | 0.100% |
| Preservatives | 0.100% |
| PEG 60 hydrogenated castor oil | 0.400% |
| Fragrances | 0.100% |
| Water        qs | 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime/regimen for treating sensitive skin, skin discomfort, tautness, itchiness or swelling of the skin, blotchy red skin, or sensations of burning or warming of the skin, comprising administering to a candidate individual in need of such treatment, for such period of time as required to elicit a skin-soothing, -calmant or anti-inflammatory response, a thus effective amount of at least one 2-amino-4-alkylaminopyrimidine 3-oxide compound.

2. The regime/regimen as defined by claim 1, comprising topically applying said effective amount of at least one 2-amino-4-alkylaminopyrimidine 3-oxide compound onto the skin of such candidate individual in need of such treatment.

3. The regime/regimen as defined by claim 1, said effective amount of at least one 2-amino-4-alkylaminopyrimidine 3-oxide compound being formulated into a physiologically acceptable vehicle, diluent or carrier therefor.

4. The regime/regimen as defined by claim 1, said at least one 2-amino-4-alkylaminopyrimidine 3-oxide compound having the structural formula (I):

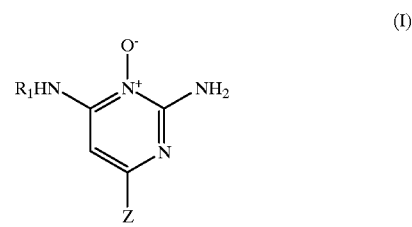

in which $R_1$ is an alkyl radical having from 1 to 20 carbon atoms, and Z is a hydrogen atom or a radical $-OR_2$, wherein $R_2$ is an alkyl radical having from 1 to 12 carbon atoms, or an acyl derivative or acid addition salt thereof.

5. The regime/regimen as defined by claim 4, wherein formula (I), $R_1$ is an alkyl radical having from 6 to 12 carbon atoms.

6. The regime/regimen as defined by claim 4, wherein formula (I), $R_2$ is an alkyl radical having from 1 to 12 carbon atoms.

7. The regime/regimen as defined by claim 4, said at least one 2-amino-4-alkylaminopyrimidine 3-oxide compound having the structural formula (I) being selected from among 2-amino-4-methylaminopyrimidine 3-oxide;
2-amino-4-ethylaminopyrimidine 3-oxide;
2-amino-4-propylaminopyrimidine 3-oxide;
2-amino-4-butylaminopyrimidine 3-oxide;
2-amino-4-pentylaminopyrimidine 3-oxide;
2-amino-4-hexylaminopyrimidine 3-oxide;
2-amino-4-heptylaminopyrimidine 3-oxide;
2-amino-4-octylaminopyrimidine 3-oxide;
2-amino-4-nonylaminopyrimidine 3-oxide;
2-amino-4-decylaminopyrimidine 3-oxide;
2-amino-4-undecylaminopyrimidine 3-oxide;
2-amino-4-dodecylaminopyrimidine 3-oxide;
2-amino-4-tridecylaminopyrimidine 3-oxide;
2-amino-4-tetradecylaminopyrimidine 3-oxide;
2-amino-4-pentadecylaminopyrimidine 3-oxide;
2-amino-4-hexadecylaminopyrimidine 3-oxide;
2-amino-4-heptadecylaminopyrimidine 3-oxide;
2-amino-4-octadecylaminopyrimidine 3-oxide;
2-amino-4-nonadecylaminopyrimidine 3-oxide;
2-amino-4-eicosadecylaminopyrimidine 3-oxide;
2-amino-4-methylamino-6-methoxypyrimidine 3-oxide;
2-amino-4-ethylamino-6-methoxypyrimidine 3-oxide;
2-amino-4-propylamino-6-methoxypyrimidine 3-oxide;
2-amino-4-butylamino-6-methoxypyrimidine 3-oxide;
2-amino-4-pentylamino-6-methoxypyrimidine 3-oxide;
2-amino-4-hexylamino-6-methoxypyrimidine 3-oxide;
2-amino-4-heptylamino-6-methoxypyrimidine 3-oxide;
2-amino-4-octylamino-6-methoxypyrimidine 3-oxide;
2-amino-4-nonylamino-6-methoxypyrimidine 3-oxide;
2-amino-4-decylamino-6-methoxypyrimidine 3-oxide;

2-amino-4-undecylamino-6-methoxypyrimidine 3-oxide;
2-amino-4-dodecylamino-6-methoxypyrimidine 3-oxide;
2-amino-4-tridecylamino-6-methoxypyrimidine 3-oxide;
2-amino-4-tetradecylamino-6-methoxypyrimidine 3-oxide;
2-amino-4-pentadecylamino-6-methoxypyrimidine 3-oxide;
2-amino-4-hexadecylamino-6-methoxypyrimidine 3-oxide;
2-amino-4-heptadecylamino-6-methoxypyrimidine 3-oxide;
2-amino-4-octadecylamino-6-methoxypyrimidine 3-oxide;
2-amino-4-nonadecylamino-6-methoxypyrimidine 3-oxide;
2-amino-4-eicosadecylamino-6-methoxypyrimidine 3-oxide;
2-amino-4-methylamino-6-ethoxypyrimidine 3-oxide;
2-amino-4-ethylamino-6-ethoxypyrimidine 3-oxide;
2-amino-4-propylamino-6-ethoxypyrimidine 3-oxide;
2-amino-4-butylamino-6-ethoxypyrimidine 3-oxide;
2-amino-4-pentylamino-6-ethoxypyrimidine 3-oxide;
2-amino-4-hexylamino-6-ethoxypyrimidine 3-oxide;
2-amino-4-heptylamino-6-ethoxypyrimidine 3-oxide;
2-amino-4-octylamino-6-ethoxypyrimidine 3-oxide;
2-amino-4-nonylamino-6-ethoxypyrimidine 3-oxide;
2-amino-4-decylamino-6-ethoxypyrimidine 3-oxide;
2-amino-4-undecylamino-6-ethoxypyrimidine 3-oxide;
2-amino-4-dodecylamino-6-ethoxypyrimidine 3-oxide;
2-amino-4-tridecylamino-6-ethoxypyrimidine 3-oxide;
2-amino-4-tetradecylamino-6-ethoxypyrimidine 3-oxide;
2-amino-4-pentadecylamino-6-ethoxypyrimidine 3-oxide;
2-amino-4-hexadecylamino-6-ethoxypyrimidine 3-oxide;
2-amino-4-heptadecylamino-6-ethoxypyrimidine 3-oxide;
2-amino-4-octadecylamino-6-ethoxypyrimidine 3-oxide;
2-amino-4-nonadecylamino-6-ethoxypyrimidine 3-oxide;
2-amino-4-eicosadecylamino-6-ethoxypyrimidine 3-oxide;
2-amino-4-methylamino-6-propyloxypyrimidine 3-oxide;
2-amino-4-ethylamino-6-propyloxypyrimidine 3-oxide;
2-amino-4-propylamino-6-propyloxypyrimidine 3-oxide;
2-amino-4-butylamino-6-propyloxypyrimidine 3-oxide;
2-amino-4-pentylamino-6-propyloxypyrimidine 3-oxide;
2-amino-4-hexylamino-6-propyloxypyrimidine 3-oxide;
2-amino-4-heptylamino-6-propyloxypyrimidine 3-oxide;
2-amino-4-octylamino-6-propyloxypyrimidine 3-oxide;
2-amino-4-nonylamino-6-propyloxypyrimidine 3-oxide;
2-amino-4-decylamino-6-propyloxypyrimidine 3-oxide;
2-amino-4-undecylamino-6-propyloxypyrimidine 3-oxide;
2-amino-4-dodecylamino-6-propyloxypyrimidine 3-oxide;
2-amino-4-tridecylamino-6-propyloxypyrimidine 3-oxide;
2-amino-4-tetradecylamino-6-propyloxypyrimidine 3-oxide;
2-amino-4-pentadecylamino-6-propyloxypyrimidine 3-oxide;
2-amino-4-hexadecylamino-6-propyloxypyrimidine 3-oxide;
2-amino-4-heptadecylamino-6-propyloxypyrimidine 3-oxide;
2-amino-4-octadecylamino-6-propyloxypyrimidine 3-oxide;
2-amino-4-nonadecylamino-6-propyloxypyrimidine 3-oxide;
2-amino-4-eicosadecylamino-6-propyloxypyrimidine 3-oxide;
2-amino-4-methylamino-6-butyloxypyrimidine 3-oxide;
2-amino-4-ethylamino-6-butyloxypyrimidine 3-oxide;
2-amino-4-propylamino-6-butyloxypyrimidine 3-oxide;
2-amino-4-butylamino-6-butyloxypyrimidine 3-oxide;
2-amino-4-pentylamino-6-butyloxypyrimidine 3-oxide;
2-amino-4-hexylamino-6-butyloxypyrimidine 3-oxide;
2-amino-4-heptylamino-6-butyloxypyrimidine 3-oxide;
2-amino-4-octylamino-6-butyloxypyrimidine 3-oxide;
2-amino-4-nonylamino-6-butyloxypyrimidine 3-oxide;
2-amino-4-decylamino-6-butyloxypyrimidine 3-oxide;
2-amino-4-undecylamino-6-butyloxypyrimidine 3-oxide;
2-amino-4-dodecylamino-6-butyloxypyrimidine 3-oxide;
2-amino-4-tridecylamino-6-butyloxypyrimidine 3-oxide;
2-amino-4-tetradecylamino-6-butyloxypyrimidine 3-oxide;
2-amino-4-pentadecylamino-6-butyloxypyrimidine 3-oxide;
2-amino-4-hexadecylamino-6-butyloxypyrimidine 3-oxide;
2-amino-4-heptadecylamino-6-butyloxypyrimidine 3-oxide;
2-amino-4-octadecylamino-6-butyloxypyrimidine 3-oxide;
2-amino-4-nonadecylamino-6-butyloxypyrimidine 3-oxide;
2-amino-4-eicosadecylamino-6-butyloxypyrimidine 3-oxide; and the branched isomers thereof.

8. The regime/regimen as defined by claim 7, said at least one 2-amino-4-alkylaminopyrimidine 3-oxide compoung having the structural formula (I) being selected from among
2-amino-4-hexylaminopyrimidine 3-oxide;
2-amino-4-octylaminopyrimidine 3-oxide;
2-amino-4-dodecylaminopyrimidine 3-oxide;
2-amino-4-octylamino-6-butyloxypyrimidine 3-oxide.

9. The regime/regimen as defined by claim 8, said at least one 2-amino-4-alkylaminopyrimidine 3-oxide compound having the structural formula (I) being selected from between 2-amino-4-dodecylaminopyrimidine 3-oxide and 2-amino-4-octylamino-6-butyloxypyrimidine 3-oxide.

10. The regime/regimen as defined by claim 2, comprising maintaining said effective amount of said at least one 2-amino-4-alkylaminopyrimidine 3-oxide compound on the skin and/or scalp of the candidate individual in need of such treatment, for such period of time as required to elicit the desired therapeutic effect, and optionally rinsing same therefrom.

11. The regime/regimen as defined by claim 4, wherein the 2-amino-4-alkylaminopryrimidine 3-oxide is selected from
2-amino-4-pentylaminopyrimidine 3-oxide;
2-amino-4-hexylaminopyrimidine 3-oxide;

2-amino-4-heptylaminopyrimidine 3-oxide;
2-amino-4-octylaminopyrimidine 3-oxide;
2-amino-4-nonylaminopyrimidine 3-oxide;
2-amino-4-decylaminoprimidine 3-oxide;
2-amino-4-undecylaminopyrimidine 3-oxide;
2-amino-4-dodecylaminopyrimidine 3-oxide;
2-amino-4-tridecylaminopyrimidine 3-oxide;
2-amino-4-tetradecylaminopyrimidine 3-oxide;
2-amino-4-pentadecylaminopyrimidine 3-oxide;
2-amino-4-hexadecylaminopyrimidine 3-oxide;
2-amino-4-heptadecylaminopyrimidine 3-oxide;
2-amino-4-octadecylaminopyrimidine 3-oxide;
2-amino-4-nonadecylaminopyrimidine 3-oxide;
2-amino-4-eicosadecylaminopyrimidine 3-oxide;
2-amino-4-pentylamino-6-methoxypyrimidine 3-oxide;
2-amino-4-hexylamino-6-methoxypyrimidine 3-oxide;
2-amino-4-heptylamino-6-methoxpyrimidine 3-oxide;
2-amino-4-octylamino-6-methoxypyrimidine 3-oxide;
2-amino-4-nonylamino-6-methoxypyrimidine 3-oxide;
2-amino-4-decylamino-6-methoxypyrimidine 3-oxide;
2-amino-4-pentylamino-6-methoxypyrimidine 3-oxide;
2-amino-4-hexylamino-6-methoxypyrimidine 3-oxide;
2-amino-4-heptylamino-6-methoxypyrimidine 3-oxide;
2-amino-4-octylamino-6-methoxypyrimidine 3-oxide;
2-amino-4-nonylamino-6-methoxypyrimidine 3-oxide;
2-amino-4-decylamino-6-methoxypyrimidine 3-oxide;
2-amino-4-undecylamino-6-methoxypyrimidine 3-oxide;
2-amino-4-dodecylamino-6-methoxypyrimidine 3-oxide;
2-amino-4-tridecylamino-6-methoxypyrimidine 3-oxide;
2-amino-4-tetradecylamino-6-methoxypyrimidine 3-oxide;
2-amino-4-pentadecylamino-6-methoxpyrimidine 3-oxide;
2-amino-4-hexadecylamino-6-methoxypyrimidine 3-oxide;
2-amino-4-heptadecylamino-6-methoxypyrimidine 3-oxide;
2-amino-4-octadecylamino-6-methoxypyrimidine 3-oxide;
2-amino-4-nonadecylamino-6-methoxypyrimidine 3-oxide;
2-amino-4-eicosadecylamino-6-methoxypyrimidine 3-oxide;
2-amino-4-pentylamino-6-ethoxypyrimidine 3-oxide;
2-amino-4-hexylamino-6-ethoxypyrimidine 3-oxide;
2-amino-4-heptylamino-6-ethoxypyrimidine 3-oxide;
2-amino-4-octylamino-6-ethoxypyrimidine 3-oxide;
2-amino-4-nonylamino-6-ethoxypyrimidine 3-oxide;
2-amino-4-decylamino-6-ethoxypyrimidine 3-oxide;
2-amino-4-undecylamino-6-ethoxypyrimidine 3-oxide;
2-amino-4-dodecylamino-6-ethoxypyrimidine 3-oxide;
2-amino-4-tridecylamino-6-ethoxypyrimidine 3-oxide;
2-amino-4-tetradecylamino-6-ethoxypyrimidine 3-oxide;
2-amino-4-pentadecylamino-6-ethoxypyrimidine 3-oxide;
2-amino-4-hexadecylamino-6-ethoxypyrimidine 3-oxide;
2-amino-4-heptadecylamino-6-ethoxypyrimidine 3-oxide;
2-amino-4-octadecylamino-6-ethoxypyrimidine 3-oxide;
2-amino-4-nonadecylamino-6-ethoxypyrimidine 3-oxide;
2-amino-4-eicosadecylamino-6-ethoxypyrimidine 3-oxide;
2-amino-4-pentylamino-6-propyloxypyrimidine 3-oxide;
2-amino-4-hexylamino-6-propyloxypyrimidine 3-oxide;
2-amino-4-heptylamino-6-propyloxypyrimidine 3-oxide;
2-amino-4-octylamino-6-propyloxypyrimidine 3-oxide;
2-amino-4-nonylamino-6-propyloxypyrimidine 3-oxide;
2-amino-4-decylamino-6-propyloxypyrimidine 3-oxide;
2-amino-4-undecylamino-6-propyloxypyrimidine 3-oxide;
2-amino-4-dodecylamino-6-propyloxypyrimidine 3-oxide;
2-amino-4-tridecylamino-6-propyloxypyrimidine 3-oxide;
2-amino-4-tetradecylamino-6-propyloxypyrimidine 3-oxide;
2-amino-4-pentadecylamino-6-propyloxypyrimidine 3-oxide;
2-amino-4-hexadecylamino-6-propyloxypyrimidine 3-oxide;
2-amino-4-heptadecylamino-6-propyloxypyrimidine 3-oxide;
2-amino-4-octadecylamino-6-propyloxypyrimidine 3-oxide;
2-amino-4-nonadecylamino-6-propyloxypyrimidine 3-oxide;
2-amino-4-eicosadecylamino-6-propyloxypyrimidine 3-oxide;
2-amino-4-pentylamino-6-butyloxypyrimidine 3-oxide;
2-amino-4-hexylamino-6-butyloxypyrimidine 3-oxide;
2-amino-4-heptylamino-6-butyloxypyrimidine 3-oxide;
2-amino-4-octylamino-6-butyloxypyrimidine 3-oxide;
2-amino-4-nonylamino-6-butyloxypyrimidine 3-oxide;
2-amino-4-decylamino-6-butyloxypyrimidine 3-oxide;
2-amino-4-undecylamino-6-butyloxypyrimidine 3-oxide;
2-amino-4-dodecylamino-6-butyloxypyrimidine 3-oxide;
2-amino-4-tridecylamino-6-butyloxypyrimidine 3-oxide;
2-amino-4-tetradecylamino-6-butyloxypyrimidine 3-oxide;
2-amino-4-pentadecylamino-6-butyloxypyrimidine 3-oxide;
2-amino-4-hexadecylamino-6-butyloxypyrimidine 3-oxide;
2-amino-4-heptadecylamino-6-butyloxypyrimidine 3-oxide;
2-amino-4-octadecylamino-6-butyloxypyrimidine 3-oxide;
2-amino-4-nonadecylamino-6-butyloxypyrimidine 3-oxide;
2-amino-4-eicosadecylamino-6-butyloxypyrimidine 3-oxide; and branched isomers thereof.

12. a regime/regimen for treating sensitive skin of the scalp of the scalp, skin discomfort, tautness, itchness or swelling of the skin, blotchy red skin, or sensations of burning or warming of the skin, comprising administering to the scalp of a candidate individual in need of such treatment, for such period of time as required to elicit a skin-soothing, -calmant or anti-inflammatory response, a thus effective amount of at least one 2-amino-4-alkylaminopyrimidine 3-oxide compound.

13. A cosmetic/dermatological composition suited for soothing or calming a variety of afflictions/conditions of human skin and/or scalp, comprising an effective amount of at least one 2-amino-4-alkylaminopyrimidine 3-oxide compound having the structural formula (I):

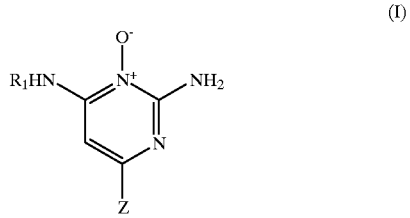

wherein $R_1$ is an alklyl radical having from 6 to 20 carbon atoms, and Z is a hydrogen atom or a radical —$OR_2$, wherein $R_2$ is an alkyl radical having from 1 to 12 carbons atoms, or an acyl derivative or acid addition salt thereof formulated into a topically applicable, physiologically acceptable vehicle, diluent or carrier therefor.

14. The cosmetic/dermatological composition as defined by claim 13, comprising from 0.01% to 20% by weight of said at least one 2-amino-4-alkylaminopyrimidine 3-oxide compound.

15. The cosmetic/dermatological composition as defined by claim 13, comprising from 0.05% to 10% by weight of said at least one 2-amino-4-alkylaminopyrimidine 3-oxide compound.

16. The cosmetic/dermatological composition as defined by claim 13, formulated as a thickened lotion, gel, emulsion, cream, aerosol, or vapor.

17. The cosmetic/dermatological composition as defined by claim 13, further comprising an effective amount of at least one surfactant, thickener, gelling agent, cosmetic agent, preservative, acidifying or basifying agent.

18. The cosmetic/dermatological composition as defined by claim 13, further comprising an effective amount of at least one skin-soothing/calmant agent other than a 2-amino-4-alkylaminopyrimidine 3-oxide, keratolytic agent, free-radical scavenger, plant, marine or bacterial extract, phospholipid, linoleic acid, linolenic acid, salicylic acid or derivative thereof, hydroxycarboxylic or ketocarboxylic acid or ester thereof, carotenoid, eicosatetraenoic acid or eicosatrienoic acid or ester or amide thereof, vitamin D or derivative thereof.

* * * * *